(12) United States Patent
Molenda et al.

(10) Patent No.: US 8,865,145 B2
(45) Date of Patent: Oct. 21, 2014

(54) WATER-IN-OIL EMULSION COMPOSITION FOR HAIR

(75) Inventors: Michael Molenda, Frankfurt (DE); Ilka Tietjen, Ilvesheim (DE)

(73) Assignee: KAO Germany GmbH, Darmstadt (DE)

( * ) Notice: Subject to any disclaimer, the term of this patent is extended or adjusted under 35 U.S.C. 154(b) by 248 days.

(21) Appl. No.: 13/128,042

(22) PCT Filed: Nov. 17, 2009

(86) PCT No.: PCT/EP2009/008175
§ 371 (c)(1),
(2), (4) Date: May 6, 2011

(87) PCT Pub. No.: WO2010/057615
PCT Pub. Date: May 27, 2010

(65) Prior Publication Data
US 2011/0293551 A1 Dec. 1, 2011

(30) Foreign Application Priority Data

Nov. 18, 2008 (EP) .................................. 08020069

(51) Int. Cl.
| | | |
|---|---|---|
| *A61Q 5/12* | (2006.01) | |
| *A61K 8/06* | (2006.01) | |
| *A61K 8/891* | (2006.01) | |
| *A61K 8/894* | (2006.01) | |
| *A61K 8/58* | (2006.01) | |
| *A61K 8/898* | (2006.01) | |

(52) U.S. Cl.
CPC . *A61K 8/898* (2013.01); *A61K 8/06* (2013.01); *A61K 8/891* (2013.01); *A61K 8/894* (2013.01); *A61Q 5/12* (2013.01); *A61K 8/585* (2013.01); *A61K 8/064* (2013.01)
USPC ...................................................... 424/70.12

(58) Field of Classification Search
CPC ......... A61K 8/06; A61K 8/891; A61K 8/894; A61K 8/585; A61K 8/064; A61K 8/898; A61Q 5/12
See application file for complete search history.

(56) References Cited

U.S. PATENT DOCUMENTS

| 6,602,494 | B1 | 8/2003 | Jahedshoar | |
| 7,223,385 | B2 | 5/2007 | Gawtrey | |
| 7,763,241 | B2 * | 7/2010 | Steigerwald et al. | 424/70.6 |
| 2009/0185994 | A1 * | 7/2009 | Bistram | 424/70.11 |

FOREIGN PATENT DOCUMENTS

| EP | 1598047 A1 * | 11/2005 | .............. A61K 7/13 |
| GB | 2149806 A * | 6/1985 | .............. A61K 7/13 |
| WO | 01/00141 A1 | 1/2001 | |
| WO | 02/11684 A2 | 2/2002 | |
| WO | 02/053112 A1 | 7/2002 | |

OTHER PUBLICATIONS

Dow Corning, Dow Corning Silicone Solutions Protect Hair from Curling Tongs and Straightening Irons, Observatory of Plastic, May 18, 2009.*
Univar, Retrieved online [Sep. 21, 2012], Retrieved from URL:<http://www.univareurope.com/downloads/703_Spain_PList_042008.pdf> and Translation.*
International Search Report Dated Mar. 12, 2010.

* cited by examiner

*Primary Examiner* — Frederick Krass
*Assistant Examiner* — Nannette Holloman
(74) *Attorney, Agent, or Firm* — Norris McLaughlin & Marcus, P.A.

(57) ABSTRACT

Present invention is related to conditioning composition for hair especially suited for leave-in application in water-in-oil (W/O) emulsion form. The object of the present invention is water in oil emulsion composition for hair comprising at least one oil, at least one silicone surfactant. at least one alkoxylated and hydroxylated amino silicone and water.

12 Claims, No Drawings

WATER-IN-OIL EMULSION COMPOSITION FOR HAIR

This application is a 371 application of PCT/EP2009/008175 filed Nov. 17, 2009, which claims foreign priority benefit under 35 U.S.C. §119 of European Application No. 08020069.4 filed Nov. 18, 2008.

Present invention is related to conditioning composition for hair especially suited for leave-in application in water-in-oil (W/O) emulsion form.

Conditioning compositions have been known for many years. Recently leave-in conditioning compositions have especially become popular because of easiness of application. Water based leave-in conditioning compositions are available in various forms such as gel, emulsion, spray conditioner etc. W/O emulsions have also been proposed recently. For example, U.S. Pat. No. 6,602,494 B1 is on transparent water in silicone hair conditioning agent comprising a silicone surfactant, a hydrophobic non-surfactant silicone compound, a cationic compound, a non-ionic silicone free surfactant a polyhydric alcohol and an electrolyte. According to the document, compositions comprise maximum 50% by weight of water phase.

WO 02/11684 A2 disclose water in oil emulsion compositions comprising polyalkylene glycol styling agents.

U.S. Pat. No. 7,223,385 B2 is on aqueous conditioning composition comprising cationic surfactants and aminated silicones. The document is silent on W/O emulsion.

The compositions disclosed in above mentioned documents either focus on product appearance such as transparency or hair feeling such as after application hair does not look or feel greasy.

Additionally it has been observed that there is a great need for compositions conditioning damaged hair especially when level of damage is variable in length of hair i.e. root is healthy, medium part is slightly damaged by colouring and environmental effects and tips are strongly damaged by colouring and permanent shaping and environmental effects. Such type of hair is extremely difficult to condition after cleansing as it usually looks uncared i.e. is difficult to comb through, has less shine, feels not soft and natural upon touching, has overwhelmingly fly-away, does not have natural elasticity and often appears like a bunch of wool.

Present inventors have surprisingly found out that a composition comprising at least one silicone emulsifier, at least one alkoxylated and hydroxylated amino silicone, at least one oil and water conditions hair and especially damaged hair satisfactorily and improves at least one of the properties mentioned above.

Accordingly, the first object of the present invention is water in oil emulsion composition for hair comprising at least one oil, at least one silicone surfactant, at least one alkoxylated and hydroxylated amino silicone and water.

Further object of the present invention is use of a water in oil emulsion composition comprising at least one oil, at least one silicone surfactant, at least one alkoxylated and hydroxylated amino silicone and water for conditioning hair.

Still further object of the present invention is use of a water in oil emulsion composition comprising at least one oil, at least one silicone surfactant, at least one alkoxylated and hydroxylated amino silicone and water for improving hair at least one hair property selected from combability, shine, elasticity, reducing fly-away, natural and soft feeling, attractive appearance.

Further object of the present invention is a process for conditioning hair wherein hair is washed with a cleansing composition based on at least one surfactant and rinsed off and towel dried, and optionally dried and afterwards and water in oil emulsion composition comprising at least one oil, at least one silicone surfactant, at least one alkoxylated and hydroxylated amino silicone and water is applied onto hair and without rinsing off hair is dried.

As from the above it is clear that the aminated silicone according to the present invention comprises hydroxyl and alkoxyl groups in the same molecule. The aminated silicones comprising only hydroxyl group as terminal group and only alkoxyl groups as terminal group are not within the meaning of the present invention.

Composition of the present invention comprises at least one oil. In principal any oil is suitable of natural and synthetic origin. Synthetic ones are preferred. Especially preferred are silicone oils and fatty acid alkyl esters.

Concentration of at least one oil component is in the range of 15 to 50%, preferably 20 to 45%, more preferably 20 to 40% and most preferably 20 to 35% by weight calculated to total composition. The concentrations mentioned herewith are at the same time total oil concentrations in the compositions.

Suitable natural oil components are almond oil, olive oil, Passiflora oil (*Passiflora edulis, Passiflora incarnate*), Black cumin oil (*Nigella sativa*), Borage oils (*Borage officinalis*), Evening Primrose oil (*Oenotera biensis*), Grapeseed oil (*Vitis vinifera*), Hempseed oil (*Cannabis sativa*), Kukui nut oil (*Aleurites moluccans*), Rosehip oil (*Rosa moschata*), Safflower oil (*Carthamus tinctorius*), Walnut oil (*Juglans nigra*) and Wheatgerm oil (*Triticum vulgare*). In the preferred from of the present invention natural oil is comprised at lower concentration ranges such as 0.1 to 1% by weight calculated to total composition.

Synthetic oils are preferred and especially preferred are silicone oils and fatty acid alkyl esters, especially $C_1$-$C_6$ alkyl esters.

Suitable fatty acid alkyl esters are according to the general formula

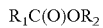

$$R_1C(O)OR_2$$

wherein $R_1$ is straight or branched, saturated or unsaturated alkyl chain with 8 to 22 C atoms, preferably 10 to 20 C atoms and more preferably 12 to 18 C atoms and $R_2$ is straight or branched, saturated or unsaturated alkyl chain with 1 to 22 C atoms, preferably 1 to 6 C atoms, more preferably 2 to 6 C atoms and most preferably 2 to 4 C atoms.

Suitable fatty acid alkyl esters are isopropyl myristate, isopropyl stearate, behenyl behenate, butyl oleate, butyloctyl palmitate, butyloctyl oleate, cetyl palmitate, cetyl laurate, cetyl myristate, cetyl oleate, cetyl stearate, decyl cocoate, decyl oleate, decyl myristate, decyl palmitate, decyl stearate, ethyl laurate, ethyl linoleate, ethyl myristate, ethyl oleate, isopropyl palmitate, isostearate, oleyl oleate, isocetyl stearate, hexyl laurate, dibutyl adipate, dioctyl adipate, myristyl myristate, oleyl erucate, stearyl oleate, stearyl myristate, stearyl stearate, stearyl cocoate, stearyl palmitate, behenyl oleate, behenyl myristate, behenyl stearate, behenyl cocoate, and behenyl palmitate.

In a further preferred from of the present invention, fatty acid alkyl esters are comprised at lower concentration ranges such as 0.1 to 2.5% by weight calculated to total composition.

In especially preferred form of the invention, composition comprises at least one silicone oil as the oil component, and in particular at least one volatile silicone oil.

Suitable silicone oils are any silicone oil liquid at ambient temperature, i.e. room temperature which is approximately 20° C. Suitable ones are dimethicones having various viscosity values as available from Dow Corning with 200 series, dimethiconols available from Dow Corning either alone or in mixture with other silicones, cyclic silicones commercially available and arylated silicones available from Dow corning under the trade name such as DC 556. In particularly preferred from of the invention composition comprise at least one volatile silicone oil and at least one non-volatile silicone oil. Nonvolatile silicone oil is preferably comprised at a lower concentration range such as 0.1 to 2.5% by weight calculated to total composition. In particularly preferred from of the inventions, compositions comprise at least one volatile silicone oil at a concentration of 15 to 50%, preferably 20 to 45%, more preferably 20 to 40% and most preferably 20 to 35% by weight calculated to total composition.

Suitable volatile silicones are dimethicones with viscosity values of approximately 1 cSt. Suitable cyclic silicones as volatile silicones are according to general formula

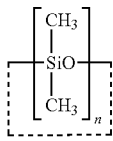

where n is a number between 3 and 7. Examples are cyclomethicone, cycloheptasiloxane, cyclohexasiloxane, cyclopentasiloxane, cyclotetrasiloxane, and cyclotrisiloxane. Among the cyclic silioxanes preferred are cyclomethicone, cyclopentasiloxane, cyclotetrasiloxane and cyclotrisiloxane. Most preferred is cyclopentasiloxane.

Composition of the present invention comprises at least one silicone surfactant. Preferably, at least one silicone surfactant is selected from PEG/PPG-3/10 Dimethicone, PEG/PPG-4/12 Dimethicone, PEG/PPG-6/4 Dimethicone, PEG/PPG-6/11 Dimethicone, PEG/PPG-8/14 Dimethicone, PEG/PPG-8/26 Dimethicone, PEG/PPG-10/2 Dimethicone, PEG/PPG-12/16 Dimethicone, PEG/PPG-12/18 Dimethicone, PEG/PPG-14/4 Dimethicone, PEG/PPG-15/5 Dimethicone, PEG/PPG-15/15 Dimethicone, PEG/PPG-16/2 Dimethicone, PEG/PPG-16/8 Dimethicone, PEG/PPG-17/18 Dimethicone, PEG/PPG-18/6-Dimethicone, PEG/PPG-18/12 Dimethicone, PEG/PPG-18/18 Dimethicone, PEG/PPG-19/19 Dimethicone, PEG/PPG-20/6 Dimethicone, PEG/PPG-20/15 Dimethicone, PEG/PPG-20/20 Dimethicone, PEG/PPG-20/23 Dimethicone, PEG/PPG-20/29 Dimethicone, PEG/PPG-22/23 Dimethicone, PEG/PPG-22/24 Dimethicone, PEG/PPG-23/6 Dimethicone, PEG/PPG-25/25 Dimethicone, PEG/PPG-27/27 Dimethicone, and PEG/PPG-30/10 Dimethicone and mixture thereof. Preferred are PEG/PPG-12/16 Dimethicone, PEG/PPG-12/18 Dimethicone, PEG/PPG-15/15 Dimethicone, PEG/PPG-17/18 Dimethicone, PEG/PPG-18/12 Dimethicone, PEG/PPG-18/12 Dimethicone, PEG/PPG-18/18 Dimethicone, PEG/PPG-19/19 Dimethicone, PEG/PPG-20/15 Dimethicone, PEG/PPG-20/20 Dimethicone, PEG/PPG-20/23 Dimethicone, PEG/PPG-20/29 Dimethicone, PEG/PPG-22/23 Dimethicone, PEG/PPG-22/24 Dimethicone, PEG/PPG-25/25 Dimethicone and PEG/PPG-27/27 Dimethicone and mixtures thereof. Particularly suitable are PEG/PPG-20/15 Dimethicone and PEG/PPG-20/15 Dimethicone and their mixture.

Concentration of one or more silicone surfactant is in the range of 0.5 to 7.5%, preferably 0.5 to 5%, more preferably 1 to 4% and most preferably 1 to 3% by weight calculated to total composition.

Composition of the present invention comprise at least one alkoxylated and hydroxylated amino silicone at a concentration of 0.01 to 10%, preferably 0.05 to 7.5% and more preferably 0.1 to 5% and most preferably 0.25 to 4% by weight, calculated to total composition.

Suitable alkoxylated and hydroxylated amino silicones are according to general formula

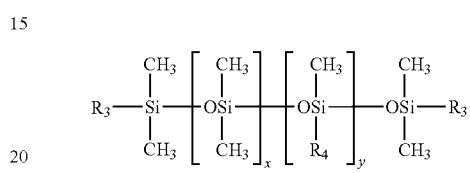

wherein R3 is hydroxyl or OR5 wherein R5 is a C1 to C4 alkyl group, R4 is a group with structure according to general formula

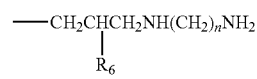

wherein R6 is a C1 to C4 alkyl and n is a 1 to 4, with the condition that R3 is partly hydroxyl group and partly OR5 group and R3 is never only hydroxyl group and only OR5 group.

Preferred compound according to above general formula is Bis-hydroxy/methoxy amodimethicone.

Compositions of the present invention comprise water, preferably at a concentration of 50% or more, more preferably 55% or more and most preferably 60% or more, by weight calculated to total composition.

In a further preferred embodiment of the present invention, composition comprises at least one water soluble electrolyte. Concentration of at least one water soluble electrolyte is preferably in the range of 0.1 to 10%, more preferably 0.25 to 7.5% and most preferably 0.5 to 5% by weight calculated to total composition.

Suitable electrolytes are known in the art such as salt of mono or divalent anion with a mono or divalent cation. Suitable ones are such as sodium chloride, sodium sulphate, magnesium chloride, calcium chloride, magnesium sulphate, potassium chloride and potassium sulphate. In particular, sodium chloride, magnesium chloride and magnesium sulphate and their mixtures are found to be most effective.

Still in a further preferred embodiment of present invention, composition comprises at least one polyol. Concentration of at least one polyol is in the range of 0.1 to 20%, preferably 0.1 to 15%, more preferably 0.25 to 10% and most preferably 0.5 to 7.5% by weight calculated to total composition.

Suitable polyols are panthenol, glycerine, (poly)ethylene and (poly)propylene glycols. Preferred are gylcerin, panthenol and (poly)propylene glycols.

Composition of the present invention preferably comprises at least one UV filter Suitable UV-absorbing substances is are ethylhexylmethoxycinnamate, 4-aminobenzoic acid and the esters and salts thereof, 2-phenyl benzimidazole-5-sulfonic acid and the alkali and amine salts thereof, 4-dimethyl aminobenzoic acid and the esters and salts thereof, cinnamic acid and the esters and salts thereof, 4-methoxycinnamic acid and the esters and salts thereof, salicylic acid and the esters and salts thereof, 2,4-dihydroxybenzophenone, 2,2',4,4'-tetrahydroxy-benzophenone, 2-hydroxy-4-methoxybenzophenone and its 5-sulfonic acid or the sodium salt thereof, 2,2'-dihydroxy-4,4'-dimethoxybenzophenone, 2-hydroxy-5-chlorobenzophenone, 2,2'-dihydroxy-4-methoxybenzophenone, 2,2'-dihydroxy-4.4'-dimethoxy-5,5'-disulfobenzo-phenone or the sodium salt thereof, 2-hydroxy-4-octyloxybenzophenone, 2-hydroxy-4-methoxy-4'-methylbenzophenone, 3-benzylidene campher, 3-(4'-sulfo)-benzylidene bornane-2-one and the salts thereof and/or 3-(4'-methyl benzylidene)-DL-campher. The amount of the UV-absorber ranges typically from about 0.01% to 7.5%, more preferably from 0.05% to 5% by weight, calculated to the total composition.

Compositions of the present invention preferably comprise at least one non-ionic surfactant. Suitable ones are alkly polyglucosides, ethoxylated fatty alcohols with various numbers of ethoxy units and the ones known with CTFA general name Polysorbate. Especially preferred are polysorbats and from them polysorbate-20.

Composition of the present invention comprises hair-conditioning agents in any type of composition. Conditioning agents can be selected from non-ionic substances, cationic amphiphilic ingredients, cationic polymers or their mixtures.

Non-ionic conditioning agents can be polyethyleneglycol mono or di fatty acid esters having general formula

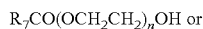

$R_7CO(OCH_2CH_2)_nOH$ or

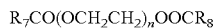

$R_7CO(OCH_2CH_2)_nOOCR_8$ wherein $R_7$ and $R_8$ are independent from each other saturated, unsaturated or branched or non-branched alkyl chain with 7 to 21 C atoms and n is typically 2-100.

In another preferred from of the present invention, compositions comprise at least one cationic conditioning agent. Cationic conditioning agents are cationic polymers and cationic surfactants. Suitable cationic polymers are those of best known with their CTFA category name Polyquaternium. Typical examples of those are Polyquaternium 1, Polyquaternium 2, Polyquaternium 4, Polyquaternium 5, Polyquaternium 6, Polyquaternium 7, Polyquaternium 8, Polyquaternium 9, Polyquaternium 10, Polyquaternium 11, Polyquaternium 12, Polyquaternium 13, Polyquaternium 14, Polyquaternium 15, Polyquaternium 16, Polyquaternium 17, Polyquaternium 18, Polyquaternium 19, Polyquaternium 20, Polyquaternium 22, Polyquaternium 24, Polyquaternium 27, Polyquaternium 28, Polyquaternium 29, Polyquaternium 30, Polyquaternium 31, Polyquaternium 32, Polyquaternium 33, Polyquaternium 34, Polyquaternium 35 and Polyquaternium 36, Polyquaternium-37, Polyquaternium 39, Polyquaternium 42, Polyquaternium 43, Polyquaternium 44, Polyquaternium 45, Polyquaternium 46, Polyquaternium 47, Polyquaternium 48, Polyquaternium-49, Polyquaternium 50, Polyquaternium 51, Polyquaternium 52, Polyquaternium 53, Polyquaternium 54, Polyquaternium 55, Polyquaternium 56, Polyquaternium 57, Polyquaternium 58, Polyquaternium 59, Polyquaternium 60, Polyquaternium 61, Polyquaternium 62, Polyquaternium 63, Polyquaternium 64, Polyquaternium 65, Polyquaternium 66, Polyquaternium 67, Polyquaternium 68, Polyquaternium 69, Polyquaternium-70, Polyquaternium 71, Polyquaternium 72, Polyquaternium 73, Polyquaternium 74, Polyquaternium 75, Polyquaternium 76, Polyquaternium 77, Polyquaternium 78, Polyquaternium-79, Polyquaternium 80, Polyquaternium 81, Polyquaternium 82, Polyquaternium 83, Polyquaternium 84, Polyquaternium 85, Polyquaternium 86 and Polyquaternium 87.

As well those polymers known with their CTFA category name Quaternium are suitable. Those are for example Quaternium-8, Quaternium-14, Quaternium-15, Quaternium-18, Quaternium-22, Quaternium-24, Quaternium-26, Quaternium-27, Quaternium-30, Quaternium-33, Quaternium-53, Quaternium-60, Quaternium-61, Quaternium-72, Quaternium-78, Quaternium-80, Quaternium-81, Quaternium-81, Quaternium-82, Quaternium-83 and Quaternium-84.

It has further been found out that especially those of cationic cellulose type polymers known as Polymer JR type from Amerchol such as Polyquaternium 10 or cationic galactomannans such as cationic guar gum known with trade name Jaguar from Rhône-Poulenc which are chemically for example Guar hydroxypropyl trimonium chloride and cationic tam gum an its derivatives known with INCI name Caesalpinia spinosa hydroxypropyltrimonium chloride, are preferred ones. Furthermore, chitosan and chitin can also be included in the compositions as cationic natural polymers. In this context reference is also made to the cationic polymers disclosed in DE 25 21 960, 28 11 010, 30 44 738 and 32 17 059, as well as to the products described in EP-A 337 354 on pages 3 to 7. It is also possible to use mixtures of various cationic polymers.

The most preferred cationic polymers are those of cationic cellulose and its derivatives, cationic guar gum and its derivatives, cationic *Caesalpinia spinosa* gum and its derivatives, polyquaternium 6, polyquaternium 7, polyquaternium 67 and polyquaternium 70.

The cationic polymers also include the quaternized products of graft polymers from organopolysiloxanes and polyethyl oxazolines described in EP-A 524 612 and EP-A 640 643.

Cationic surfactants suitable for the present invention are according to the general formula

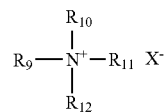

where $R_9$ is a saturated or unsaturated, branched or straight alkyl chain with 8-22 C atoms or

$R_{13}CONH(CH_2)_n$ where $R_{13}$ is saturated or unsaturated, branched or straight alkyl chain with 7-21 C atoms and n has value of 1-4, or

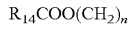

$R_{14}COO(CH_2)_n$ where $R_{14}$ is saturated or unsaturated, branched or straight alkyl chain with 7-21 C atoms and n has value of 1-4, and $R_{10}$ is hydrogen or unsaturated or saturated, branched or straight alkyl chain with 1-22 C atoms or

$R_{13}CONH(CH_2)_n$ or

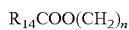

$R_{14}COO(CH_2)_n$ where $R_{13}$, $R_{14}$ and n are same as above.

$R_{12}$ and $R_{13}$ are hydrogen or lower alkyl chain with 1 to 4 carbon atoms, and X is anion such as chloride, bromide, methosulfate.

Typical examples of those ingredients are cetyltrimethyl ammonium chloride, steartrimonium chloride, behentrimonium chloride, stearamidopropyl trimonuim chloride, dioleoylethyl dimethyl ammonium methosulfate, dioleoylethyl hydroxyethylmonium methosulfate.

Amido amines may as well be used as a conditioning cationic surfactant in the compositions of the present invention. Typical non-limiting example is stearoxypropyldimethylamine, stearamidopropyldimethylamine known with a trade name Lexamine S13 from Inolex and behenamidopropyl dimethyl amine available under the trade name Amidet APA 22 from Kao Chemicals.

The compositions according to the invention may also comprise further conditioning substances such as protein hydrolyzates and polypeptides, e.g., keratin hydrolyzates, collagen hydrolyzates of the type "Nutrilan®" or elastin hydrolyzates, as well as also in particular plant protein hydrolyzates, optionally, cationized protein hydrolyzates, e.g., "Gluadin®".

Typical concentration range for any of those conditioners of cationic polymers and cationic surfactants is in the range of 0.01-10% by weight, preferably 0.01-7.5% by weight, more preferably 0.05-5% and most preferably 0.1-5% by weight calculated to the total composition.

In a further preferred from of the invention, compositions comprise at least one polyphenol or mixture of polyhenols which is included into compositions of the present invention from a natural plant extract. In principal any natural plant extract rich of polyphenols is suitable within the meaning of the present invention. Within the meaning of the present invention the extracts are liquid extracts and prepared by mixing plant parts such as leaves, fruits, blossoms and roots with a solvent such as water, alcohol, propyleneglycol or mixture of more than one solvent and incubating for certain period of time and filtrating the undissolved plant parts. Suitable aqueous (e.g. steam-distilled) alcoholic or hydro-alcoholic plant extracts known per se are in particular aloe, pineapple, artichoke, arnica, avocado, valerian, bamboo, henbane, birch, stinging nettle, echinacea, ivy, wild angelica, gentian, ferns, pine needles, silver weed, ginseng, broom, oat, rose hip, hamamelis, hay flowers, elderberry, hop, coltsfoot, currants, chamomile, carrots, chestnuts, clover, burr root, cocoanut, cornflower, lime blossom, lily of the valley, marine algae, balm, mistletoe, passion flower, ratanhia, marigold, rosemary, horse chestnut, pink hawthorn, sage, horsetail, yarrow, primrose, nettle, thyme, walnut, wine leaves, white hawthorn, etc. Suitable trade products are, for example, the various "Extrapon®" products, "Herbasol®", "Sedaplant®" and "Hexaplant®". Extracts and the preparation thereof are also described in "Hagers Handbuch der pharmazeutischen Praxis", 4$^{th}$ Ed. Preferred plant extracts are prepared from *Vitis vinifera, Malus domestica, Camelia sinensis, Juglans regia, Ribes Uva-Crispa, Ribes nigrum, Ribes rubum* and *Citrus aurantiifolia*. The above mentioned extracts may also be available in the powder form and such are also suitable within the meaning of the present invention.

The polyphenol comprising extracts are included into the compositions of the present invention at a concentration of 0.001 to 10%, preferably 0.005 to 7.5%, more preferably 0.01 to 5% and most preferably 0.05 to 2.5% by weight, calculated to total composition based on dry matter of the extract.

Composition comprises organic solvents such as ethanol, propanol, isopropanol, benzyl alcohol, benzyloxyethanol, ethoxydiglycol, alkylene carbonates such as ethylene carbonate and propylene carbonate, phenoxyethanol, butanol, isobutanol, cyclohexane, cyclohexanol, hexyleneglycol, ethylene carbonate, ethylene glycol monoethylether, ethylene glycol monobutyl ether, ethylene glycol monophenyl ether, 1-phenylethylalcohol, 2-phenylethylalcohol, o-methoxyphenol. Concentration of organic solvents should not exceed 10% by weight, preferably in the range of 0.1 to 7.5% by weight calculated to total composition.

The compositions of present invention can comprise active ingredients such as sequestering agents, natural ingredients, flavonoids, ceramides, pyrrolidone carboxylic acid or its salts and its esters with an alkyl chain etc.

The sequestering agents are selected from polycarboxy acids. The preferred one is ethylene diamine tetraacetic acid, EDTA. Typical useful concentration range for sequestering agents is of 0.01-2.5% by weight calculated to the total composition.

Natural plant extracts may be incorporated usually in an amount of about 0.01% to about 10%, preferably 0.05% to 7.5%, in particular 0.1% to 5% by weight, calculated as dry residue thereof to the total composition. Suitable aqueous (e.g. steam-distilled) alcoholic or hydro-alcoholic plant extracts known per se are in particular extracts from leaves, fruits, blossoms, roots, rinds or stems of aloe, pineapple, artichoke, arnica, avocado, valerian, bamboo, henbane, birch, stinging nettle, echinacea, ivy, wild angelica, gentian, ferns, pine needles, silver weed, ginseng, broom, oat, rose hip, hamamelis, hay flowers, elderberry, hop, coltsfoot, currants, chamomile, carrots, chestnuts, clover, burr root, cocoanut, cornflower, lime blossom, lily of the valley, marine algae, balm, mistletoe, passion flower, ratanhia, marigold, rosemary, horse chestnut, pink hawthorn, sage, horsetail, yarrow, primrose, nettle, thyme, walnut, wine leaves, white hawthorn, etc. Suitable trade products are, for example, the various "Extrapon®" products, "Herbasol®", "Sedaplant®" and "Hexaplant®". Extracts and the preparation thereof are also described in "Hagers Handbuch der pharmazeutischen Praxis", 4$^{th}$ Ed.

Compositions of the present invention optionally may comprise at least one flavone and/or its derivative at a concentration in the range of 0.01% to 2%, by weight, preferably 0.01 to 1.5% and more preferably 0.05 to 1.0% by weight, calculated to total composition.

Suitable non-limiting examples are t-flavanone, quercetin, morin, taxifoline, isoquercetin, rutin, chatechin, epichatechin and luteolin, The most preferred ones are t-flavanone (trans 3,4'-dimethylflavanonol), quercetin and morin. The flavone and its derivatives are incorporated into the compositions of the present invention either as commercially available pure (the word pure should not be taken as 100% purity and should be understood as flavone derivative enriched raw materials containing other substances) raw material and as well as in the form of natural extracts such as green tea extract, gingko extract, etc.

Composition of the present invention may optionally comprise at least one pyrrolidon carboxylic acid ester. The alkyl chain length in the ester group, in the preferred form, is between 8 and 20 C atoms, more preferably between 12 and 18 C atoms and most preferably between 14 and 18 C atoms.

Some examples to the suitable pyrrolidon carboxylic acid ester are with the alkyl chain of methyl, ethyl, n-propyl, isopropyl, n-butyl, iso butyl, n-hexyl, n-octyl, n-nonyl, n-decyl, ethylhexyl, methylhexyl, capryl, lauryl myristyl, cetyl, octyldodecyl, isostearyl, stearyl, arachidyl, behenyl, oleyl, linoleyl, benzyl, phenoxyethyl. Preferred are n-octyl, n-nonyl, n-decyl, ethylhexyl, methylhexyl, capryl, lauryl myristyl, cetyl, octyldodecyl, stearyl, isostearyl, arachidyl, behenyl, oleyl and linoleyl. More preferred are lauryl myristyl, cetyl, octyldodecyl, stearyl, isostearyl, arachidyl, behenyl, oleyl, and linoleyl. Particularly preferred pyrrolidon carboxylic acid ester is octyldodecyl pyrrolidon carboxylic acid which is available under the trade name Protelan ODPC from Zschimmer & Schwarz.

Concentration of at least one pyrrolidon carboxylic acid ester in the compositions of the present invention is in the range of 0.01 to 5% by weight calculated to total composition. It should be noted that compositions of the present invention can comprise more than one pyrrolidon carboxylic acid ester such as 2 or 3. The above mentioned concentrations refer to the total concentration of the pyrrolidon carboxylic acid esters.

Composition of the present invention comprises pyrrolidon carboxylic acid and/or its salts. In principal any pyrrolidon carboxylic acid salt is suitable within the meaning of the present invention. Suitable examples are aluminium, calcium, copper, magnesium, potassium, sodium and zinc salts of pyrrolidon carboxylic acid. Preferred are aluminium, calcium, magnesium, potassium and sodium salts and more preferred are sodium and potassium salts. The most preferred is sodium salt.

Concentration of pyrrolidon carboxylic acid and/or its salts is in the range of 0.01 to 10% by weight calculated to the total composition. Concentrations mentioned here refer to the total concentration of the pyrrolidon carboxylic acid and/or its salts present in the compositions.

According to the preferred embodiment of the present invention, at least one pyrrolidone carboxylic acid ester of the above formula and pyrrolidone carboxylic acid and/or its salts are comprised in the composition of the present invention at a weight ratio of 1:100 to 1:1, preferably 1:75 to 1:2, more preferably 1:50 to 1:3 and most preferably 1:25 to 1:5.

Further in preferred embodiment of the present invention, compositions comprise at least one dyestuff either for colouring the composition and/or colouring hair. Suitable direct dyes are of cationic, anionic and neutral nitro dyes. It should be noted that they can also be used in combination with each other. In other words, a composition according to present invention can comprise an anionic and a cationic dye as well as an anionic and a nitro dye or a cationic and a nitro dye. Certainly the combination of all three dyestuffs is also possible.

Any cationic direct dye is in principal suitable for the compositions. Examples are Basic Blue 6, Basic Blue 7, Basic Blue 9, Basic Blue 26, Basic Blue 41, Basic Blue 99, Basic Brown 4, Basic Brown 16, Basic Brown 17, Natural Brown 7, Basic Green 1, Basic Orange 31, Basic Red 2, Basic Red 12 Basic Red 22, Basic Red 51, Basic Red 76, Basic Violet 1, Basic Violet 2, Basic Violet 3, Basic Violet 10, Basic Violet 14, Basic Yellow 57 and Basic Yellow 87.

Any anionic dye is in principal suitable for the compositions. Anionic dyes are especially preferred for colouring the composition and used at relatively low concentrations. Suitable examples are such as Acid Black 1, Acid Blue 1, Acid Blue 3, Food Blue 5, Acid Blue 7, Acid Blue 9, Acid Blue 74, Acid Orange 3, Acid Orange 6, Acid Orange 7, Acid Orange 10, Acid Red 1, Acid Red 14, Acid Red 18, Acid Red 27, Acid Red 50, Acid Red 52, Acid Red 73, Acid Red 87, Acid Red 88, Acid Red 92, Acid Red 155, Acid Red 180, Acid Violet 9, Acid Violet 43, Acid Violet 49, Acid Yellow 1, Acid Yellow 23, Acid Yellow 3, Food Yellow No. 8, D&C Brown No. 1, D&C Green No. 5, D&C Green No. 8, D&C Orange No. 4, D&C Orange No. 10, D&C Orange No. 11, D&C Red No. 21, D&C Red No. 27, D&C Red No. 33, D&C Violet 2, D&C Yellow No. 7, D&C Yellow No. 8, D&C Yellow No. 10, FD&C Red 2, FD&C Red 40, FD&C Red No. 4, FD&C Yellow No. 6, FD&C Blue 1, Food Black 1, Food Black 2, Disperse Black 9 and Disperse Violet 1 and their alkali metal salts such as sodium, potassium.

Among those, the preferred anionic dyestuffs are Acid Red 52, Acid Violet 2, Acid Red 33, Acid Orange 4, Acid Red 27 and Acid Yellow 10 and their salts. The most preferred anionic dyes are Acid Red 52, Acid Violet 2, Acid Red 33, Acid Orange 4 and Acid Yellow 10, and their salts Neutral dyes, so called nitro dyes for shading purposes are also optionally contained in the compositions. Suitable ones are HC Blue No. 2, HC Blue No. 4, HC Blue No. 5, HC Blue No. 6, HC Blue No. 7, HC Blue No. 8, HC Blue No. 9, HC Blue No. 10, HC Blue No. 11, HC Blue No. 12, HC Blue No. 13, HC Brown No. 1, HC Brown No. 2, HC Green No. 1, HC Orange No. 1, HC Orange No. 2, HC Orange No. 3, HC Orange No. 5, HC Red BN, HC Red No. 1, HC Red No. 3, HC Red No. 7, HC Red No. 8, HC Red No. 9, HC Red No. 10, HC Red No. 11, HC Red No. 13, HC Red No. 54, HC Red No. 14, HC Violet BS, HC Violet No. 1, HC Violet No. 2, HC Yellow No. 2, HC Yellow No. 4, HC Yellow No. 5, HC Yellow No. 6, HC Yellow No. 7, HC Yellow No. 8, HC Yellow No. 9, HC Yellow No. 10, HC Yellow No. 11, HC Yellow No. 12, HC Yellow No. 13, HC Yellow No. 14, HC Yellow No. 15, 2-Amino-6-chloro-4-nitrophenol, picramic acid, 1,2-Di-amino-4-nitrobenzol, 1,4-Diamino-2-nitrobenzol, 3-Nitro-4-aminophenol, 1-Hydroxy-2-amino-3-nitrobenzol and 2-hydroxyethylpicramic acid.

Concentration of one or more direct dyes in total is in the range of 0.00001 to 5% by weight, preferably 0.00002 to 4% more preferably 0.00005 to 3% and most preferably 0.0001 to 2.5% by weight calculated to total composition. It should be noted that dyestuff concentration is especially low when dyes are used for colouring the composition. In case hair dyeing is the purpose, the dye concentration is usually 0.01% and above, by weight calculated to total composition.

Optical brightener are preferably used in the compositions of the present invention at a concentration of 0.01 to 1% by weight, calculated to total composition. Suitable and especially preferred is disodium distyrylbiphenyl disulphonate available under trade name Tinopal CBS-x from Ciba Speciality chemicals.

Compositions of the present invention can also comprise synthetic mica as a further shine enhancer. Use of synthetic mica coated with metal oxide or oxides mainly in decorative cosmetics is disclosed in an international patent application of Sun Chemical Corporation published with a number WO 2005/065632 A1. In the document synthetic mica and coated synthetic mica with at least one metal oxide or oxides is disclosed in detail, the content of the document is included herewith by reference.

Suitable metal oxide or oxides for coating synthetic mica are titanium dioxide, chromium oxide, ferric oxide or mixtures thereof. In the present invention the preferred is synthetic mice coated with titanium dioxide. Such materials are commercially available from Sun Chemical Corporation and known with their INCI names Synthetic Fluorphologopite.

The particle size distribution of synthetic mica coated with a metal oxide or oxides is in the range of 1 to 750 μm, preferably 1 to 250 μm, more preferably 1 to 100 μm and most preferably 20 to 95 μm. The particle sizes referred are relating to the volume particle size distribution meaning that particles found in the coated synthetic mica having volume particle size in the given ranges.

Concentration of synthetic mica coated with at least metal oxide or oxides is from 0.001 to 10%, preferably 0.05 to 7.5%, more preferably 0.1 to 5% and most preferably 0.2 to 2.5% by weight calculated to total composition.

Further additional compounds may be present in the permanent shaping compositions of the present invention is ubiquinone of the formula

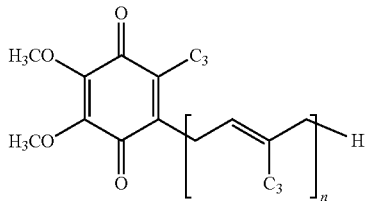

where n is a number between 1 and 10. Preferred ubiquinones are the ones where n is a number between 6 and 10 and especially preferred is Ubiquinone 50 where n is 10, also known as Coenzyme Q10. Concentration ubiquinone of the above formula in permanent shaping compositions of the present invention is from 0.0001 to 1%, preferably from 0.0002 to 0.75%, more preferably from 0.0002 to 0.5% and most preferably from 0.0005 to 0.5% by weight, calculated to total composition.

It has further been found out that the compositions of the present invention are not rinsed off after application onto hair. Furthermore, the compositions are applied onto freshly shampooed and towel dried hair and without rinsing off, hair is dried. The application of the inventive compositions of the present invention is not excluded from the scope.

Thus, present invention is also a process for conditioning hair wherein a composition comprising comprises at least one oil, at least one silicone surfactant, at least one alkoxylated/hydroxylated amino silicone and water is applied onto freshly shampooed and towel dried hair and without rinsing off hair is dried.

Following examples is to illustrate the invention, but not to limit it.

EXAMPLE 1

|  | % by weight |
| --- | --- |
| Cyclopentasiloxane | 25 |
| Bis-hydroxy/methoxy amodimethicone | 1 |
| PEG/PPG-20/15 Dimethicone | 2 |
| Preservative, fragrance | q.s. |
| Water | to 100 |

The above composition was prepared as follows: Cyclopentasiloxane, Bis-hydroxy/methoxy amodimethicone, and PEG/PPG-20/15 Dimethicone are mixed in a vessel and water was added while mixing at ambient temperature. Afterwards, the mixture was homogenized with Ulrathorax at 11,000 rpm for 3 min per kg (only for laboratory scale).

The above composition is used on hair having various degrees of damage in length and gave her optimal conditioning, in terms of elasticity, shine, combing and volume.

EXAMPLE 2

|  | % by weight |
| --- | --- |
| Cyclopentasiloxane | 15 |
| Trisiloxane | 15 |
| Bis-hydroxy/methoxy amodimethicone | 1 |
| PEG/PPG-20/15 Dimethicone | 2 |
| Propyleneglycol | 5 |
| Preservative, fragrance | q.s. |
| Water | to 100 |

Similar conditioning effects as in Example 1 were observed with the above composition.

EXAMPLE 3

|  | % by weight |
| --- | --- |
| Cyclopentasiloxane | 20 |
| Dimethicone 1 cSt | 5 |
| Isopropyl myristate | 0.5 |
| Wheatgerm oil | 0.1 |
| Bis-hydroxy/methoxy amodimethicone | 1.5 |
| PEG/PPG-20/15 Dimethicone | 1.6 |
| Propyleneglycol | 3 |
| Preservative, fragrance | q.s. |
| Water | to 100 |

Similar conditioning effects as in Example 1 were observed with the above composition.

EXAMPLE 4

|  | % by weight |
| --- | --- |
| Cyclopentasiloxane | 20 |
| Dimethicone 0.65 cSt | 5 |
| Isopropyl palmitate | 0.1 |
| Phenyltrimethicone | 0.5 |
| Wheatgerm oil | 0.1 |
| Bis-hydroxy/methoxy amodimethicone | 1.5 |
| Cetrimonium chloride | 0.2 |
| PEG/PPG-20/15 Dimethicone | 1.6 |
| Octyldodecyl pyrrolidone carboxylic acid | 0.1 |
| PCA sodium | 0.1 |
| Propyleneglycol | 3 |
| Preservative, fragrance | q.s. |
| Water | to 100 |

The above composition improved hair combability, shine, elasticity and especially hair had less flyaways after leave in application on a freshly shampooed hair.

EXAMPLE 5

|  | % by weight |
| --- | --- |
| Cyclotetrasiloxane | 12 |
| Dimethicone 0.65 cSt | 3 |
| Cylomethicone | 15 |
| Isopropyl stearate | 0.1 |
| Phenyltrimethicone | 0.5 |
| Wheatgerm oil | 0.1 |
| Bis-hydroxy/methoxy amodimethicone | 1.5 |
| Cetrimonium chloride | 0.2 |
| PEG/PPG-20/15 Dimethicone | 1.6 |
| Octyldodecyl pyrrolidone carboxylic acid | 0.1 |
| PCA sodium | 0.1 |
| Propyleneglycol | 3 |

The above compositiom improved hair combability, shine, elasticity and especially hair had less flyaways after leave in application on a freshly shampooed hair.

EXAMPLE 6

| | % by weight |
|---|---|
| Cyclotetrasiloxane | 12 |
| Dimethicone 0.65 cSt | 3 |
| Cylomethicone | 15 |
| Isopropyl stearate | 0.1 |
| Phenyltrimethicone | 0.5 |
| Wheatgerm oil | 0.1 |
| Bis-hydroxy/methoxy amodimethicone | 1.5 |
| Cetrimonium chloride | 0.2 |
| PEG/PPG-20/15 Dimethicone | 1.6 |
| Octyldodecyl pyrrolidone carboxylic acid | 0.1 |
| PCA sodium | 0.1 |
| Propyleneglycol | 3 |
| C.I. 17200/Red no 33 | 0.0008 |
| Preservative, fragrance | q.s. |
| Water | to 100 |

The above composition improved hair combability, shine, elasticity and especially hair had less flyaways after leave in application on a freshly shampooed hair. The composition had a slight purple/red colour which did not result in hair colouring.

EXAMPLE 7

| | % by weight |
|---|---|
| Cyclopentasiloxane | 20 |
| Dimethicone 0.65 cSt | 5 |
| Isopropyl palmitate | 0.1 |
| Phenyltrimethicone | 0.5 |
| Wheatgerm oil | 0.1 |
| Bis-hydroxy/methoxy amodimethicone | 1.5 |
| Cetrimonium chloride | 0.2 |
| PEG/PPG-20/15 Dimethicone | 1.6 |
| Octyldodecyl pyrrolidone carboxylic acid | 0.1 |
| PCA sodium | 0.1 |
| Propyleneglycol | 3 |
| Basic red 51 | 0.1 |
| Preservative, fragrance | q.s. |
| Water | to 100 |

The above compositiom improved hair combability, shine, elasticity and especially hair had less flyaways after leave in application on a freshly shampooed hair. The composition was red and gave hair red colour.

EXAMPLE 8

| | % by weight |
|---|---|
| Cyclopentasiloxane | 20 |
| Dimethicone 0.65 cSt | 5 |
| Isopropyl palmitate | 0.1 |
| Pentaphenyltetrasiloxane | 0.5 |
| Almond oil | 0.1 |
| Bis-hydroxy/methoxy amodimethicone | 1.5 |
| Behentrimonium chloride | 0.2 |
| PEG/PPG-20/15 Dimethicone | 1.6 |
| Octyldodecyl pyrrolidone carboxylic acid | 0.1 |
| PCA sodium | 0.1 |
| Polysilicone-15 | 0.3 |
| Propyleneglycol | 3 |
| Basic red 51 | 0.1 |
| Preservative, fragrance | q.s. |
| Water | to 100 |

The above compositiom improved hair combability, shine, elasticity and especially hair had less flyaways after leave in application on a freshly shampooed hair. The composition was red and gave hair red colour.

EXAMPLE 9

| | % by weight |
|---|---|
| Cyclopentasiloxane | 20 |
| Dimethicone 0.65 cSt | 5 |
| Isopropyl palmitate | 0.1 |
| Trimethlypentyphenyl trisiloxane | 0.5 |
| Wheatgerm oil | 0.1 |
| Ubiquinone | 0.1 |
| Bis-hydroxy/methoxy amodimethicone | 1.5 |
| Cetrimonium chloride | 0.2 |
| PEG/PPG-20/15 Dimethicone | 1.6 |
| Octyldodecyl pyrrolidone carboxylic acid | 0.1 |
| PCA sodium | 0.1 |
| Propyleneglycol | 3 |
| Preservative, fragrance | q.s. |
| Water | to 100 |

The above composition improved hair combability, shine and elasticity. Long lasting shine was especially observed on damaged hair.

EXAMPLE 10

| | % by weight |
|---|---|
| Cyclopentasiloxane | 20 |
| Dimethicone 0.65 cSt | 5 |
| Isopropyl palmitate | 0.1 |
| Phenyltrimethicone | 0.5 |
| Wheatgerm oil | 0.1 |
| Polysorbate-20 | 0.5 |
| Bis-hydroxy/methoxy amodimethicone | 1.5 |
| Cetrimonium chloride | 0.2 |
| *Vitis vinifera* | 0.1 |
| PEG/PPG-18/18 Dimethicone | 1.6 |
| Octyldodecyl pyrrolidone carboxylic acid | 0.1 |
| PCA sodium | 0.1 |
| Propyleneglycol | 3 |
| Preservative, fragrance | q.s. |
| Water | to 100 |

-continued

| | % by weight |
|---|---|
| Preservative, fragrance | q.s. |
| Water | to 100 |

-continued

| | % by weight |
|---|---|
| Cyclopentasiloxane | 20 |
| Dimethicone 0.65 cSt | 5 |

EXAMPLE 11

| | % by weight |
|---|---|
| Cyclopentasiloxane | 15 |
| Dimethicone 0.65 cSt | 10 |
| Disodium distyrylbiphenly disulphonate | 0.1 |
| Trimethylpentaphenyl trisiloxane | 1.0 |
| Wheatgerm oil | 0.1 |
| Bis-hydroxy/methoxy amodimethicone | 1.5 |
| Cetrimonium chloride | 0.2 |
| PEG/PPG-18/18 Dimethicone | 1.6 |
| Octyldodecyl pyrrolidone carboxylic acid | 0.1 |
| PCA sodium | 0.1 |
| Propyleneglycol | 3 |
| Preservative, fragrance | q.s. |
| Water | to 100 |

EXAMPLE 12

| | % by weight |
|---|---|
| Cyclopentasiloxane | 20 |
| Dimethicone 0.65 cSt | 5 |
| Isopropyl palmitate | 0.1 |
| Polyquaternium-70 | 0.1 |
| Trimethyl pentaphenyl trisiloxane | 0.3 |
| Wheatgerm oil | 0.1 |
| Bis-hydroxy/methoxy amodimethicone | 1.5 |
| Cetrimonium chloride | 0.2 |
| PEG/PPG-20/15 Dimethicone | 0.8 |
| PEG/PPG-18/18 Dimethicone | 0.8 |
| Octyldodecyl pyrrolidone carboxylic acid | 0.1 |
| PCA sodium | 0.1 |
| Propyleneglycol | 3 |
| Preservative, fragrance | q.s. |
| Water | to 100 |

The invention claimed is:

1. A water-in-oil emulsion composition, adapted for leave-in application to hair, comprising at least one oil, at least one silicone surfactant, at least one alkoxylated and hydroxylated amino silicone and water, wherein the at least one alkoxylated and hydroxylated amino silicone comprises Bis-hydroxy/methoxy amodimethicone.

2. The composition according to claim 1, wherein at least one oil is selected from volatile dimethicones and cyclic silicones according to general structure

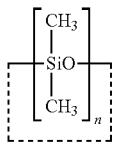

where n is a number between 3 and 7, and fatty acid alkyl esters according to the general formula $R_1C(O)OR_2$ wherein $R_1$ is straight or branched, saturated or unsaturated alkyl chain with 8 to 22 C atoms, and $R_2$ is straight or branched, saturated or unsaturated alkyl chain with 1 to 22 C atoms.

3. The composition according to claim 1, further comprising at least one oil at a concentration of 15 to 50% by weight, calculated to total composition.

4. The composition according to claim 1, wherein the at least one silicone surfactant is selected from PEG/PPG-3/10 Dimethicone, PEG/PPG-4/12 Dimethicone, PEG/PPG-6/4 Dimethicone, PEG/PPG-6/11 Dimethicone, PEG/PPG-8/14 Dimethicone, PEG/PPG-8/26 Dimethicone, PEG/PPG-10/2 Dimethicone, PEG/PPG-12/16 Dimethicone, PEG/PPG-12/18 Dimethicone, PEG/PPG-14/4 Dimethicone, PEG/PPG-15/5 Dimethicone, PEG/PPG-15/15 Dimethicone, PEG/PPG-16/2 Dimethicone, PEG/PPG-16/8 Dimethicone, PEG/PPG-17/18 Dimethicone, PEG/PPG-18/6Dimethicone, PEG/PPG-18/12 Dimethicone, PEG/PPG-18/18 Dimethicone, PEG/PPG-19/19 Dimethicone, PEG/PPG-20/6 Dimethicone, PEG/PPG-20/15 Dimethicone, PEG/PPG-20/20 Dimethicone, PEG/PPG-20/23Dimethicone, PEG/PPG-20/29 Dimethicone, PEG/PPG-22/23 Dimethicone, PEG/PPG-22/24Dimethicone, PEG/PPG-23/6 Dimethicone, PEG/PPG-25/25 Dimethicone, PEG/PPG-27/27Dimethicone, and PEG/PPG-30/10 Dimethicone and mixture thereof.

5. The composition according to claim 1, wherein the silicone surfactant is PEG/PPG-20/15 Dimethicone.

6. The composition according to claim 1, further comprising water at a concentration 50% or more by weight calculated to total composition.

7. The composition according to claim 1, further comprising at least one water soluble salt.

8. The composition according to claim 1, further comprising one or more compounds selected from UV filters, polyols, non-ionic surfactant, optical brighteners, polyphenols, and arylated silicones.

9. The composition according to claim 1, further comprising at least one hair conditioning agent selected from non-ionic compounds, cationic amphiphilic ingredients, cationic polymers and their mixtures.

10. The composition according to claim 1, further comprising at least one dyestuff.

11. The composition according to claim 1, further comprising at least one ubiquinone of the formula

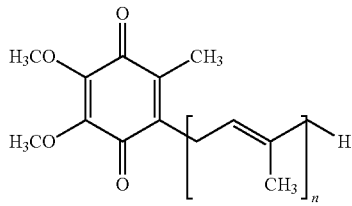

where n is a number between 1 and 10.

12. A process for conditioning hair, wherein the process comprises:
    washing hair with a cleansing composition;
    afterwards, applying the water-in-oil emulsion composition according to claim 1 onto the hair; and,
    drying the hair without rinsing off the water-in-oil composition.

* * * * *